United States Patent [19]
Paciello et al.

[11] Patent Number: 6,107,524
[45] Date of Patent: *Aug. 22, 2000

[54] PROCESS FOR PRODUCING ALDEHYDES BY HYDROFORMYLATION OF OLEFINS

[75] Inventors: Rocco Paciello, Bad Dürkheim; Heinz-Josef Kneuper, Mannheim; Bernhard Geissler, Kirchheim; Michael Röper, Wachenheim, all of Germany

[73] Assignee: BASF Aktiengesellschaft, Ludwigshafen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 09/101,692

[22] PCT Filed: Jan. 28, 1997

[86] PCT No.: PCT/EP97/00372

§ 371 Date: Jul. 15, 1998

§ 102(e) Date: Jul. 15, 1998

[87] PCT Pub. No.: WO97/28113

PCT Pub. Date: Aug. 7, 1997

[30] Foreign Application Priority Data

Jan. 30, 1996 [DE] Germany .......................... 196 03 201

[51] Int. Cl.⁷ .................................................. C07C 45/50
[52] U.S. Cl. .......................... 568/454; 568/451; 568/455
[58] Field of Search .................................. 568/451, 454, 568/455

[56] References Cited

U.S. PATENT DOCUMENTS

| | | | |
|---|---|---|---|
| 3,594,425 | 7/1971 | Brader | 260/604 |
| 3,857,895 | 12/1974 | Booth | 260/604 HF |
| 4,400,547 | 8/1983 | Dawes | 568/454 |
| 5,387,719 | 2/1995 | Kneuper et al. | 568/455 |
| 5,919,987 | 7/1999 | Kneuper et al. | 568/461 |

FOREIGN PATENT DOCUMENTS

| | | |
|---|---|---|
| 621 075 | 10/1994 | European Pat. Off. . |
| 1530136 | 6/1968 | France . |
| 26 04 545 | 12/1977 | Germany . |
| 33 38 340 | 5/1984 | Germany . |
| 252 086 | 9/1994 | Japan . |
| 82/03856 | 11/1982 | WIPO . |

OTHER PUBLICATIONS

New Syntheses with Carbon Monoxide, Falbe, pp38–100, 1980.
Chem. Ber. 102,2238 (1969).
Tetrahedron Lett., No. 29, pp3261–3266, 1968.
Hydrocarbon Process, 54, Jun. 1975, 83–91.
J. Heterocyclic Chem., 14, 191 (1977).
J. Am. Chem. Soc. 80,2745 (1958).
Recueil Trav. Chim. Pays.–Bas. 112, 351 (1993).
Chem. Ing. Tech, 44, 708 (1972).

*Primary Examiner*—Johann Richter
*Assistant Examiner*—Sreeni Padmanabhan
*Attorney, Agent, or Firm*—Keil & Weinkauf

[57] ABSTRACT

A process for the preparation of aldehydes or aldehydes and alcohols by hydroformylation of olefins containing more than 3 carbon atoms comprising a hydroformylation stage, in which the olefin is hydroformylated under a pressure of from 50 to 1000 bar and at a temperature of from 50° to 180° C. using a rhodium catalyst that is dissolved in a homogeneous reaction medium and by extraction of the rhodium catalyst, in which a) the hydroformylation is carried out in the presence of a rhodium complex, which exhibits, as ligand, a polydentate, organic nitrogen compound that is free from phosphorus and capable of forming complexes with Group VIII metals, which additionally contains at least one tertiary nitrogen radical that is capable of being protonized by a weak acid, b) the effluent of the hydroformylation stage is subjected to extraction with an aqueous solution of a distillable acid optionally following separation or partial separation of aldehydes and alcohols, c) the aqueous acid extract is subjected to thermal treatment in the presence of an organic solvent or solvent mixture, which is inert under the hydroformylation conditions, with distillation of the aqueous acid, by means of which treatment the complex is deprotonized and transferred to the organic phase, and d) the organic phase containing the catalyst complex is recycled to the hydroformylation stage.

9 Claims, 1 Drawing Sheet

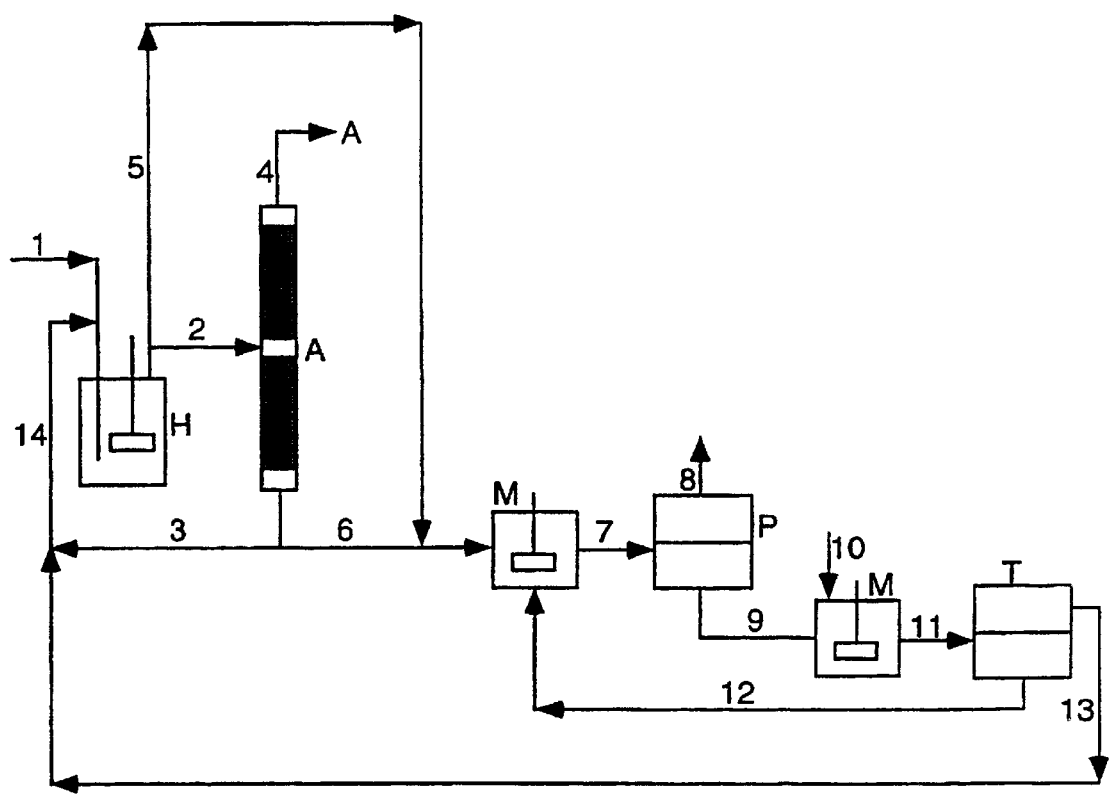

PROCESS FOR PRODUCING ALDEHYDES BY HYDROFORMYLATION OF OLEFINS

This is the U.S. National Stage Applications if PCT/EP97/00372 filed Jan. 28, 1997.

DESCRIPTION

The invention relates to a process for the preparation of aldehydes or aldehydes and alcohols by hydroformylation of olefins containing more than 3 carbon atoms and recovery of the catalyst by a combination of (1) recycling the distillation bottoms following the removal, by distillation, of the hydroformylation products and (2) extracting the catalyst complex with aqueous solutions of weak acids whose polydentate nitrogenous ligand additionally contains at least one tertiary nitrogen radical protonizable with weak acids.

The hydroformylation of olefins with carbon monoxide and hydrogen in the presence of transition metal catalysts is well known. While α-olefins are capable of hydroformylation to a high degree using rhodium-containing catalysts (cf J. Falbe, Ed.: New Syntheses With Carbon Monoxide, Springer, Berlin 1980, pp. 55 et seq), this catalyst system is less suitable for internal and internal, branched-chain olefins and also for olefins containing more than 7 carbon atoms (cf Falbe, pp. 95 et seq). Thus internal carbon-carbon double bonds are hydroformylated in the presence of such a catalyst only very slowly. Since the separation of the hydroformylation product from the homogeneous catalyst dissolved in the reaction system usually takes place by distillation and the boiling point of the aldehyde formed during hydroformylation increases with increasing carbon number and chain length to temperatures at which the rhodium-containing catalyst decomposes, this hydroformylation method is uneconomical for the hydroformylation of olefins containing more than 7 carbon atoms. In the hydroformylation of polymeric olefins such as polyisobutene, the noble metal-containing catalyst cannot be recovered in a reusable form.

On the other hand internal and internal, branched-chain olefins can be advantageously hydroformylated with so-called "bare" rhodium, ie with homogeneous rhodium compounds dissolved in the hydroformylation medium and not modified with phosphorous ligands such as phosphines or phosphites. Such rhodium catalysts not modified with phosphines or phosphites and their suitability as catalysts for the hydroformylation of the aforementioned classes of olefins are known (cf Falbe, pp. 38 et seq). The terms "bare rhodium" or "bare rhodium catalysts" are used in this application for rhodium hydroformylation catalysts which are not modified, under the conditions of the hydroformylation, with ligands and particularly not with phosphorous ligands such as phosphine or phosphite ligands, unlike conventional rhodium hydroformylation catalysts. Carbonyl or hydrido ligands are not to be regarded as ligands in this context. It is assumed in the technical literature (cf Falbe, pp. 38 et seq), that the rhodium compound $HRh(CO)_4$ is the catalytically active rhodium species in the hydroformylation using "bare rhodium catalysts", although this is not absolutely proven on account of the many chemisms concurrently taking place in the hydroformylation reaction zone. Only for the sake of simplicity do we also go by this assumption in the present application, without this imposing any restriction on the scope of the invention, if at some time in the future a rhodium species other than that stated should turn out to be the actual catalytically active species. The "bare rhodium catalysts" form under the conditions of the hydroformylation reaction from rhodium compounds, eg rhodium salts, such as rhodium(III) chloride, rhodium(III) nitrate, rhodium(III) acetate, rhodium(II) acetate, rhodium(III) sulfate, or rhodium(III) ammonium chloride, from rhodium chalkogenides, such as rhodium(III) oxide or rhodium(III) sulfide, from salts of rhodium oxyacids, for example the rhodates, from rhodium carbonyl compounds, such as $Rh_4(CO)_{12}$ and $Rh_6(CO)_{16}$ or from organorhodium compounds, such as rhodium dicarbonyl acetylacetonate, cyclooctadiene rhodium acetate or chloride in the presence of $CO/H_2$ mixtures, generally designated as synthesis gas. For information on the execution of hydroformylations with "bare" rhodium reference may be made, at this juncture, to the following literature by way of example: U.S. Pat. No. 4,400,547; DE-A 3338340; DE-A 2604545; WO 82/03856; Chem. Ber. 102, 2238 (1969); Tetrahedron Lett. 29, 3261 (1968); Hydrocarbon Process. 85–86 (1975).

However hydroformylation using "bare" rhodium also suffers from the drawback that the thermolabile rhodium catalyst (cf U.S. Pat. No. 4,400,547) partially decomposes to metallic rhodium on account of the thermal load imposed during purification, by distillation, of the hydroformylation product, which is deposited on the walls of the reactor and pipes. The precipitated metallic rhodium cannot be recycled to the hydroformylation reaction, since it cannot be converted back to the catalytically active rhodium compound under the hydrotormylation conditions. The rhodium losses resulting from this chemical behavior of "bare rhodium catalysts" have hitherto prevented any large-scale operation of this process.

DE-A 3,338,340 and U.S. Pat. No. 4,400,547 describe processes for hydroformylation using "bare rhodium catalysts", in which a phosphine or phosphite is added to the effluent of the hydroformylation for the prevention of the deposition of rhodium and to protect the rhodium catalyst from thermal disintegration during purification, by distillation, of the hydroformylation product stream by the formation of phosphine or phosphite complexes. On completion of distillation the rhodium-containing distillation bottoms are treated with an oxidizing agent, in which case the rhodium is liberated in catalytically active form from the relevant phosphine or phosphite complexes and the phosphine or phosphite ligands are oxidized to the corresponding phosphine oxides and phosphates not capable of forming rhodium complexes under the hydroformylation conditions. The oxidized distillation bottoms are then used again as catalyst for the hydroformylation. The oxidized phosphorus compounds formed during the oxidation are not usually undesirable during hydroformylation, but the peculiarities of the process are such that the oxidized phosphorus compounds accumulate in this hydroformylation circuit, for which reason a partial stream of this catalyst solution must be constantly removed from the hydroformylation circuit and replenished by fresh catalyst solution. The removed catalyst solution must be subjected to a separate procedure for the recovery the rhodium that is present therein.

WO 82/03856 relates to a process for the thermostabilization of unmodified, that is to say "bare rhodium catalysts", in which the effluent of the hydroformylation reaction is treated with an oxygen-containing gas, by which means aldehydes formed are partially oxidized to the corresponding carboxylic acids, which form thermostable rhodium carboxylates with the rhodium catalyst during purification by distillation, which carboxylates can be reused as catalysts for the hydroformylation. A disadvantage of this process is the reduction of the yield as a result of the partial oxidation of the desired aldehyde to carboxylic acids. Furthermore this process is restricted to those hydroformylations in which distillable products are formed. Thus, for example, in this process, the rhodium catalyst cannot be separated from the hydroformylation product of polyisobutene.

Hydroformylations with inter alia cobalt and rhodium in the presence of polydentate, nitrogenous ligands containing at least two nitrogen radicals, such as bipyridine and N,N,N',N'-tetramethylethylenediamine, are described in U.S. Pat. No. 3,594,425. These ligands effect stabilization of the catalyst during purification by distillation with subsequent catalyst recycling, in the so-called "residues mode". On completion of the distillation the rhodium-containing distillation bottoms are used again as catalyst for the hydroformylation. The high-boilers formed during the hydroformylation and by distillative purification are not usually undesirable during hydroformylation, but the peculiarities of the process are such that the oxidized phosphorus compounds accumulate in this hydroformylation circuit, for which reason a partial stream of this catalyst solution must be constantly removed from the hydroformylation circuit and replenished by fresh catalyst solution. The removed catalyst solution must be subjected to a separate procedure for the recovery of the rhodium present therein.

Furthermore this process is restricted to those hydroformylations in which distillable products are formed. Thus, for example, in this process, the rhodium catalyst cannot be separated from the hydroformylation product of polyisobutene.

Rhodium complexes with polydentate, nitrogenous ligands are also described as catalysts for hydroformylations in JP-A 262,086 (1994). A high selectivity toward branched-chain products is reported to be a special property of such systems.

U.S. Pat. No. 4,298,499 describes the introduction of nitrogenous ligands such as bipyridine to an oxo-effluent, with the intention of preventing precipitation of rhodium during the purification by distillation. The hydroformylation itself was carried out in the presence of a tertiary amine for specific formation of alcohols. Following the extraction of the amine, the introduction of inter alia nitrogenous ligands is intended to effect separation of rhodium without deposition of rhodium. The distillation bottoms are then recycled as catalyst to the hydroformylation zone. However, this suffers from the aforementioned drawback of the "residues mode", namely the necessity to remove a portion of the residues which has to be worked up to recover the rhodium.

Finally, EP 621,075 reveals a reversible extraction of tert amine-substituted triaryl phosphines. In particular, said reference describes an extraction using aqueous solutions containing carbonic acids. Depressurization of the solution again yielded a catalyst which is soluble in the organic medium. This concept of the use of amine-substituted aryl phosphines is encumbered with drawbacks, since, firstly, side reactions such as the oxidation of triaryl phosphine to triaryl phosphine oxide using rhodium catalysts in the presence of $CO_2$ are known and, secondly, yield losses caused by double bond isomerization are to be expected. Finally, internal double bonds are hydroformylated by Rh/phosphine only very slowly. Further, the tert amine-substituted phosphines are difficult to prepare It is thus an object of the present invention to find a process for the preparation of aldehydes from internal and/or branched-chain olefins using "bare rhodium catalysts", which does not suffer from the above drawbacks and by means of which the said problems relating to the deposition of metallic rhodium during purification, by distillation, of the hydroformylation product and the separation of rhodium catalyst from undistillable desired aldehydes or from high-boilers peculiar to the reaction can be satisfactorily solved.

The invention solves this problem by means of a process for the preparation of aldehydes or aldehydes and alcohols by hydroformylation of olefins containing more than 3 carbon atoms, including a hydroformylation stage, in which the olefin is hydroformylated under a pressure of from 50 to 1000 bar and at a temperature of from 50° to 180° C. using a rhodium catalyst that is dissolved in a homogeneous reaction medium, and a catalyst recovery stage involving extraction of the rhodium catalyst, in which a) the hydroformylation is carried out in the presence of a rhodium complex which contains, as ligand, a polydentate, organic nitrogen compound that is free from phosphorus and capable of forming complexes with Group VIII metals, which compound additionally contains at least one tertiary nitrogen radical that is capable of being protonized by a weak acid, b) the effluent of the hydroformylation stage, is subjected, optionally following separation or partial separation of aldehydes and alcohols, to extraction with an aqueous solution of a distillable acid, c) the aqueous acid extract is subjected to heat treatment in the presence of an organic solvent or solvent mixture which is inert under the hydroformylation conditions, with distillation of the aqueous acid, by means of which treatment the complex is deprotonized and transferred to the organic phase, and d) the organic phase containing the catalyst complex is recycled to the hydroformylation stage.

This novel process surprisingly yields excellent results not only as regards the simple method of catalyst recovery, but also on account of the high yields of aldehydes compared with alcohols, even at low hydroformylation temperatures, whereas it would have been expected from U.S. Pat. No. 4,298,499 and Chem. Ing. Techn. 44, 708, (1972) that the aldehyde yield would, in the presence of ligands containing tert-amine groups, be relatively small and thus not sufficient for a large-scale process.

According to the invention, the ligands used are primarily bifunctional polydentate organic nitrogen compounds containing at least two nitrogen atoms capable of forming a complex with Group VIIIB transition metals and which additionally contain at least one tertiary amine group capable of being protonized.

Due to the action of these ligands there are formed coordinate bonds with the central rhodium atom of the rhodium catalyst—presumably via the free electron pairs of the nitrogen atoms. Such compounds are known as chelating agents. The presence of at least one tertiary amino group which is protonizable and is not attached to the central rhodium atom of the rhodium catalyst, is a determining factor for the feasibility of the process of the invention.

In particular, use is made of the novel compounds of the formula 1:

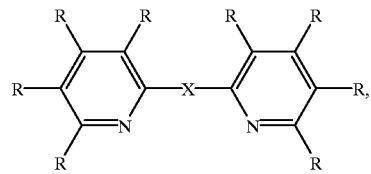

In which X denotes a bridging member selected from the group consisting of a covalent bond, methylene, ethylene, oxo, thio, alkylimino, and arylimino and the radicals R independently denote hydrogen, alkyl radicals containing from 1 to 18 carbon atoms, or alkoxy radicals containing from 1 to 18 carbon atoms, where these radicals can be part of a saturated or unsaturated ring and where at least one of the radicals R or optionally of the substituents on a ring formed by the alkyl or alkoxy radicals is a radical of the formula:

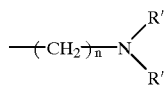

in which n denotes an integer from 0 to 20 and R' denotes alkyl, cycloalkyl, aralkyl, or aryl radicals containing up to 18 carbon atoms, where the radicals R' can be bridged together.

Other suitable ligands are polyamines of the formula 2:

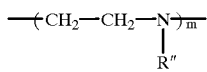

where R" denotes hydrogen alkyl, cycloalkyl, aryl, or aralkyl radicals, which can in turn carry dialkylamino radicals and m denotes an integer from 2 to 35000, provided that when R" denotes hydrogen at least some of the hydrogen atoms are substituted by alkyl carbonyl containing from 2 to 18 carbon atoms or by hydroxy(alkoxy)alkyl radicals obtained by the reaction of the secondary amino group with from 1 to 10 mol of ethylene oxide or from 1 to 10 mol of propylene oxide and further provided that the polyamine contains at least 3 tertiary nitrogen atoms that are capable of being protonized.

Particularly preferred are tert-amine-substituted bipyridines of the formula 3:

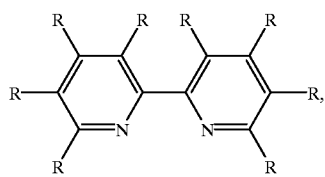

in which the radicals R have the meanings stated for formula 1 and which carry at least one radical containing a tertiary amino group and having the formula:

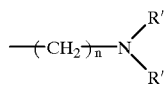

in which n and R' have the aforementioned meanings.

Representative examples are the ligands 1 and 2 and their positional isomers 1' and 2' and also compounds substituted by further inert substituents.

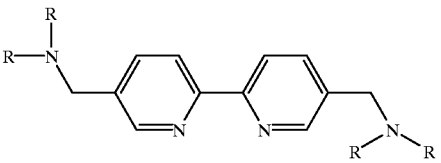

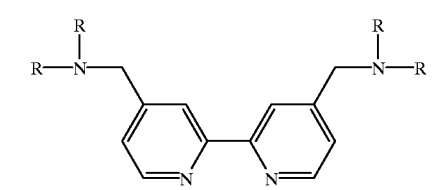

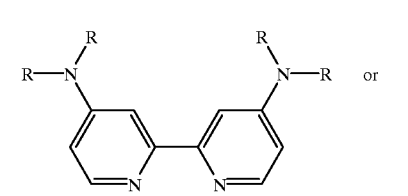

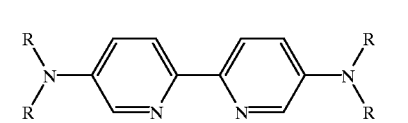

To illustrate the large number of ligands to be used in the process of the invention a number of further nitrogenous chelating agents is mentioned below by way of example, which can be used in the process of the invention following the introduction of an additional tertiary amino group. 2,2'-Biquinolines such as ligand 3:

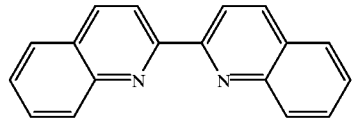

5,6,5',6'-Dibenzo-2,2'-biquinolines such as ligand 4:

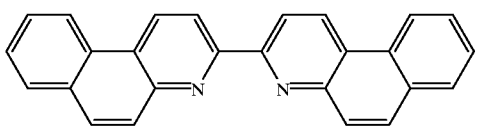

1,10-Phenanthrolines, 2,9-dimethyl phenanthrolines, 4,7-diphenyl-1,10-phenanthrolines, such as ligand 5 ("bathophenanthroline"):

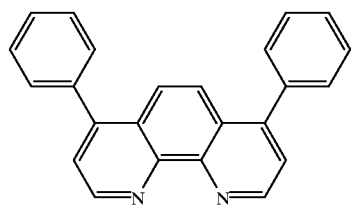

2,9-Dimethyl-4,7-diphenyl-1,10-phenanthrolines such as ligand 6 ("bathocuproine"):

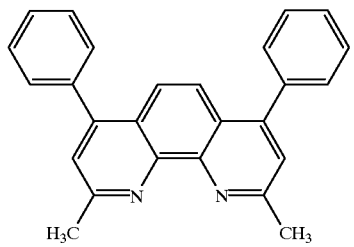

4,5-Diazofluorenes such as ligand 7:

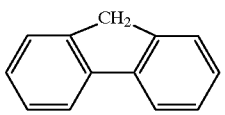

Dipyrido-(3,2-a:2',3'-c)phenazines such as ligand 9:

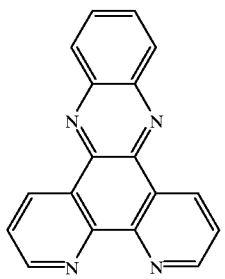

(ligands 7 and 8 can be obtained as described in Aust. J. Chem., 23, 1023, (1970))

2,2',6',2''-Terpyridines such as ligand 9:

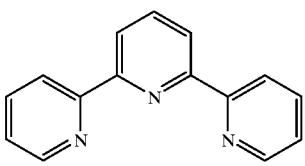

4'-Phenyl-2,2',6',2''-terpyridines such as ligand 10:

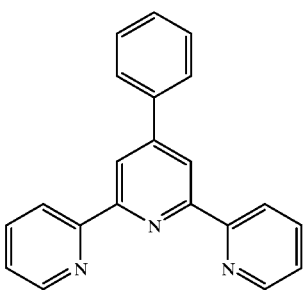

4-Methyl-(4'-phenyl)-(4''-methyl)-2,2',6',2''-terpyridines such as ligand 11:

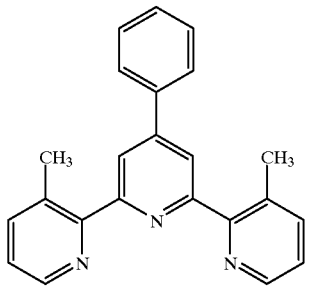

Other suitable polydentate ligands containing nitrogen are bipyrroles, bipyrazoles, bisimidazoles, bitriazoles, bitetrazoles, bipyridazines, bipyrimidines, bipyrazines, bitriazines, and also the porphines. The ligands can be asymmetrical, if desired, for example produced by linking an imidazole to a pyridine. The hydroformylation with the rhodium complex with the polydentate nitrogenous ligands takes place under known conditions. It is generally carried out at temperatures ranging from 60 to 180° C., preferably from 80 to 140° C., and more preferably from 90 to 130° C. and under a pressure generally of from 50 to 1000 bar, preferably from 70 to 500 bar, and more preferably from 100 to 400 bar. The hydroformylation otherwise takes place under conditions as are usually used for hydroformylations using "bare" rhodium and as are described for example in the literature cited above relating to hydroformylation using "bare" rhodium.

The pressure and temperature conditions used in the hydroformylation stage and the composition of the synthesis gas can be varied to influence the product ratio alcohol/aldehyde in the hydroformylation product stream for example, for given synthesis gas compositions—molar ratio of $CO:H_s$ 50:50, 40:60 and 60:40 respectively—, the hydroformylation of trimerpropylene—carried out at a temperature of 130° C. and under a pressure of 280 bar—there is attained a molar ratio of aldehyde to alcohol of 93:7 in each case. When the temperature is increased from 130° C. to 150° C. the molar ratio of aldehyde to alcohol in the hydroformylation product stream changes as a function of the synthesis gas composition—$CO:H_2$ molar ratio 50:50, 40:60, and 60:40—to 76:24, 67:33, and 82:18 respectively.

The hydroformylation can be carried out in the presence or absence of organic solvents. The use of organic solvent is particularly advantageous, especially in the hydroformylation of long-chain or polymeric olefins. The solvents used can be those usually employed in hydroformylation processes, for example high-boiling aromatic and aliphatic hydrocarbons or high-boiling aldehyde condensation products formed during the hydroformylation reaction as by-products resulting from the condensation of the aldehydes produced.

The effluent from the hydroformylation stage is conveniently depressurized prior to its extraction with the aqueous acid phase. The extraction of the hydroformylation product stream is generally carried out at temperatures ranging from 20° to 140° C., preferably from 70° to 130° C. and more preferably from 90° to 120° C. and under a pressure of generally from 1 to 20 bar, preferably from 1 to 10 bar and more preferably from 1 to 5 bar. The extraction can be carried out in air or under an inert gas atmosphere, for example an atmosphere of nitrogen, hydrogen, or argon. However, it may be advantageous to add carbon monoxide or synthesis gas to the inert gas used or to carry out the extraction in the presence of carbon monoxide.

During extraction the ratio by volume of aqueous to organic phase is generally adjusted to from 0.2:1 to 2:1 and preferably from 0.3:1 to 1:1. The content of water-soluble, polymeric extracting agents in the aqueous acidic phase is generally from 0.1 to 50%, preferably from 1 to 30% and more preferably from 3 to 10%.

During extraction with the acidic aqueous phase there protonizition takes place at the tertiary amino group of the ligand, by which means the rhodium complexes become water-soluble.

The extracting agents used for the process of the invention are aqueous solutions of distillable acids, particularly distillable acids whose ammonium salts can be dissociated back to free ligand and free acid at temperatures between room temperature and 200° C.

Particularly suitable extracting agents are aqueous solutions of acids whose $pK_s$ value is 3 to 6. Specific examples thereof are carbonic acid, formic acid, acetic acid, propionic acid, n-butyric acid, or valeric acid. In the case of carbonic acid, the organic liquid which contains the catalyst and which is to be extracted is mixed with water as described in EP 0,621,075 and carbonic acid gas is forced in. Following phase separation, the desired phase is worked up as described for the other acids.

Suitable apparatus for the extraction of the hydroformylation product stream with the aqueous acidic phase comprises virtually all liquid-liquid extractors, for example mixer-settlers, bubble-cap columns, or counter-flow or parallel-flow extracting columns, where these can be equipped with additional internal fittings to improve the efficiency of mixing of the aqueous and organic phases, for example sieve trays, filling material, or static mixers. The extraction of the rhodium catalyst from the hydroformylation product stream can be carried out in a single stage, but preferably a multistage extraction is used, for example a two-stage or three-stage extraction, in which the aqueous phase containing the chelating agent organic phase is caused to flow parallel to or, more preferably, countercurrently to the organic phase.

On completion of the extraction the hydroformylation product stream freed from rhodium catalyst can be purified in conventional manner, for example by distillation, in order to isolate the desired alcohols and/or aldehydes present therein.

In order to liberate the rhodium complexes dissolved in the aqueous extract and to transfer them to an organic phase which can be recycled to the hydroformylation, there is added to the aqueous acidic extract a solvent suitable for the hydroformylation, for example a liquid hydrocarbon or a hydrocarbon mixture such as Texanol® sold by Eastman. Products of the hydroformylation which are suitable for use as solvents or by-products of the hydroformylation are equally suitable. The ratio by volume of the solvent to the aqueous phase is usually from 0.2:1 to 2:2 and preferably from 0.5:1 to 1:1 the mixture of solvent and aqueous acid phase is then heated to temperatures such that the ammonium salt of the weak acid is dissociated and the, deprotonized rhodium complex is dissolved in the solvent. Following separation of the organic phase from the aqueous phase, if present, the organic phase now containing the rhodium catalyst is recycled to the hydroformylation stage.

The deprotonization usually takes place with thorough mixing of the organic and aqueous phases and heating up to, say, 90° C. for the removal of $CO_2$ or up to, say, 150° C. for the removal of carboxylic acids, whilst a temperature of 200° C. need not generally be exceeded.

A detailed description of an advantageous embodiment of the process of the invention is given below with reference to FIG. 1 by way of example. Obvious details not necessary for illustration of the process of the invention have been omitted from FIG. 1 for the sake of clarity.

The embodiment shown in FIG. 1 of the process of the invention embraces the process stages of hydroformylation using a rhodium catalyst homogeneously dissolved in an organic reaction medium, the separation of the catalyst from the effluent of the hydroformylation reaction, and the return of the rhodium removed from said hydroformylation effluent to the hydroformylation stage. The isolation of the catalyst takes place optionally following partial or complete distillation by reversible extraction of the catalyst from the said effluent or distillation bottoms using an acidic, aqueous phase. Subsequent thermal dissociation of the acid/ligand adduct following extraction, the catalyst is retransferred to an organic phase, by which means the recovery of the rhodium without salt formation is guaranteed. The rhodium is then recycled to the hydroformylation stage. When the process is carried out continuously, it is convenient to carry out catalyst isolation by distillation alone until the by-products accumulate to such an extent that extraction becomes necessary.

Specifically, in a continuous embodiment of the process of the invention as illustrated in FIG. 1, the hydroformylation effluent of the hydroformylated olefin 1 coming from the hydroformylation reactor H following depressurization and separation of the liquid phase from excess synthesis gas is passed either through line 5 to be subjected to extraction processing or through line 2 to be previously subjected to a distillation processing stage (consisting of flash equipment and/or a column). The distillation processing stage A causes more readily boiling aldehydes 4 to be separated from high-boiling catalyst-containing bottoms. The bottoms are intermittently or partially passed to the extraction stage via line 6 and intermittently or partially passed through line 6 to a stage involving purification by extraction. In said extraction stage an acidic aqueous phase is mixed with the organic phase in a mixer M. This mixture is fed through line 7 to a phase-separating stage P. The organic phase comprising aldehydes and/or high-boiling components is separated via line 8 and is available for further processing. The aqueous phase is passed through line 9 to a mixer M, where it is mixed with an organic phase 10 which can be tolerated by the hydroformylation reaction and which comprises, for example, olefins, aldehydes, and/or alcohols, toluene or other aromatics or blends such as Texanol®, or ethers such as diethyl ether. This mixture is then fed through line 11 to be subjected to thermal dissociation in stage T. This may be effected, for example, by means of a distillation column to cause separation of the water/carboxylic acid mixture, or by pure thermal treatment to eliminate $CO_2$. The aqueous phase can, if desired, be recycled to the extraction stage via line 12, or it can be removed from the system. The catalyst-containing organic phase is recycled to the hydroformylation stage via line 13 the process of the invention is particularly well suited for the hydroformylation of olefins containing more than 3, and preferably more than 7 carbon atoms, in particular for the hydroformylation of $C_7$–$C_{20}$ olefins, which can be straight-chain or branched-chain and which can contain α-olefinic and/or internal double bonds, eg octene-1, dodecene-1, trimer- and tetramer-propylene, or dimer-trimer- and tetramer-butylenes. Similarly, unsaturated oligomers of other olefins can be hydroformylated. Likewise different co-oligomers of different olefins. The aldehydes formed from these olefins serve, eg, as intermediates for the preparation of plasticizer alcohols and surfactants, which can be produced therefrom in conventional manner by hydrogenation. The olefins used for the hydroformylation can be obtained eg by the acid-catalyzed elimination of water from the corresponding fatty alcohols or according to a large number of other technical processes as are described, for example, in Weissermel, Arpe: Industrielle Organische Chemie, pp 67–86, Verlag Chemie, Weinheim, 1978. The process of the invention is also particularly well suited for the hydroformylation of polymeric olefins, for example low molecular weight polyisobutene, low molecular weight polybutadiene or low molecular weight poly(1,3-butadiene-co-isobutene) or poly(1,3-butadiene-co-butene). By "low molecular weight polymers" we mean in particular polymers having molecular weights of from 280 bis 5000° alton. It is also possible, however, to hydroformylate unsaturated polymers of higher molecular weight, ie having molecular weights above 5000. The only prerequisite for this is that they must be soluble in the hydroformylation medium.

The present process is thus suitable for the preparation of virtually all aldehydes which are obtainable via the hydroformylation of olefins. In particular for example, substituted olefins, which can generally carry one or two, but preferably one substituent, can also be hydroformylated by the process of the invention. For example unsaturated aliphatic carboxylates, acetals, alcohols, ethers, aldehydes, ketones, and amines and amides can be hydroformylated by the process of the invention. Those substituted starting olefins which are of interest are, eg, methacrylates, dicyclopentadiene, vinyl ether, and allyl ether and in particular corresponding substituted derivatives of unsaturated fatty acids, for example the esters of oleic, linoleic, linolenic, ricinic, or erucic acid. The aldehydes which can be obtained from these olefinic raw materials by hydroformylation are likewise starting materials for the preparation of biologically readily degradable, surface-active substances.

EXAMPLES

A) syntheses of catalyst precursors: 5,5'-bis(dimethylaminomethyl)-2,2'bipyridine (ligand 1) is prepared from β-picoline in three stages:

1st stage:
the oxidative linkage of 4-picoline to form 4,4'-dimethyl-2,2'-bipyridine is described in J. Chem. Soc., Dalton Trans., 1985, pp. 2247.the linkage of β-picoline to form 5,5'-dimethyl-2,2'-bipyridine takes place in a very similar manner and was carried out as described in said reference.

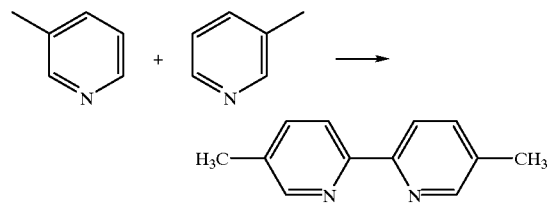

2nd stage:
the free radical bromination of 6,6'-dimethyl-2,2'-bipyridine in CCl$_4$ in the presence of a radical starter such as benzoyl peroxide is described in Helv. Chim. Acta., Vol. 67, pp. 2264, 1984. The bromination of 5,5'-dimethyl-2,2'-bipyridine with N-bromosuccinimide in the presence of 2,2-azodiisobutyronitrile acting as radical starter takes place in a very similar manner and was carried out as described in said reference.

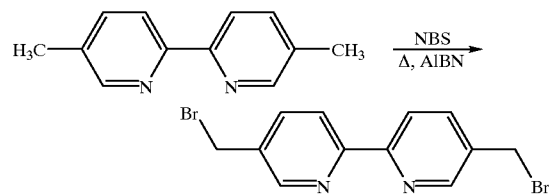

3rd stage:
5,5'-bis(bromomethyl)-2,2'-bipyridine was then caused to react with LiNMe$_2$ in THF to produce 5,5'-bis(dimethylaminomethyl)-2,2'-bipyridine. The solution was quenched with a 1% strength NaHCO$_3$ solution and ethyl ether added until a second phase had formed the purification of the organic phase yielded the ligand 1.

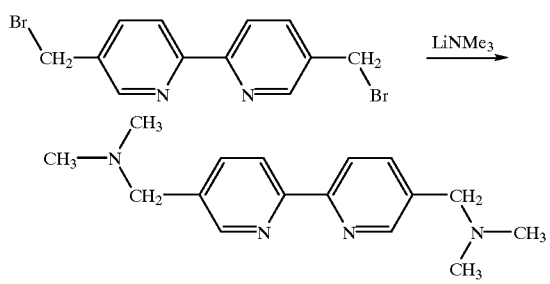

Alternatively and in analogy to stage 1 a linkage of 4-dimethylaminopyridine to produce 4,4'-bis(dimethylamino)-2,2'-bipyridine is also possibly.

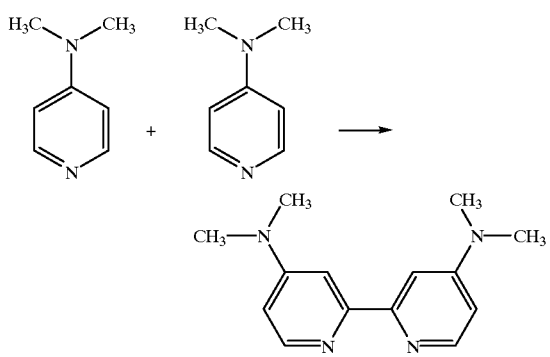

B) General conditions of a batch procedure:

All of the batch hydroformylations effected under a pressure of 70 bar were carried out in an autoclave having a capacity of 100 mL (material HC). The reaction mixture was heated to reaction temperature over a period of 10 min, whilst the solution was stirred vigorously with a gas/liquid stirrer. All of the batch hydroformylations effected under a pressure of 280 bar were carried out in an autoclave having a capacity of 300 mL (material HC). The reaction mixture was heated to reaction temperature over a period of 45 min and the solution was stirred vigorously with a magnetic stirrer. The desired pressure was in both cases adjusted by means of CO/H$_2$ (1:1), the pressure in the reactor being kept at a constant level during the reaction by forcing in more gas as required via a pressure regulator. On conclusion of the reaction the autoclave was cooled, depressurized, and emptied. An analysis of the reaction mixture was carried out by means of GC—using an internal standard and correction factors.

Example 1

Hydroformylation with Rh/ligand 1 and separation by extraction with acetic acid solutions and catalyst recycling A) In the known hydroformylation of octene-N (isooctene mixture, degree of branching 1,3; 98 g) with rhodium/ligand 1 (13 ppm of Rh, L/Rh=10, 150° C., 280 bar of $CO/H_2$ 1:1, 5 h, using 5 g of Texanol® acting as solvent) there was obtained a conversion of octenes of 98%, a yield of 76% nonanal and of 19% nonanol at a 3% balance loss (based on octene-N).

B) Separation by distillation of the oxo-products at 20 mbar up to a base temperature of 150° C.

C) Repetition of step 1 (12 ppm of Rh), rhodium catalyst/bottoms solution from (b) being used. A conversion of octenes of 99% and a yield of 66% nonanal and 15% nonanol were obtained at a 16% balance loss (based on octene-N: mechanical losses, formation of high-boilers and paraffin included).

D) Separation by distillation of the oxo-products (99 g) under a pressure of 20 mbar up to a base temperature of 150° C. (16 g), extraction of the bottoms with 5% strength acetic acid (1:1 by volume)) followed by phase separation. The phase separation was accelerated by filtration over a kieselguhr bed and a paper filter. 15 ppm of Rh were found in the organic phase, ie rhodium was extracted with 80% efficiency. Following the introduction of Texanol® to the aqueous phase followed by the evaporation of acetic acid/water under standard pressure up to a base temperature of 150° C. there was obtained a homogeneous solution.

E) Repetition of step 1 (12 ppm of Rh), a rhodium catalyst/Texanol® solution from (d) being used. An octene conversion of 97%, a yield of nonanal of 67%, and a yield of nonanol of 10.5% was achieved at a 19% balance loss (based on octene-N). The direct high-boiler analysis by separation, by distillation, of the oxo-products at a temperature of 150° C. and under a pressure of 20 mbar indicated only 5% of high-boilers.

F) On carrying out direct extraction of the effluent with 5% strength acetic acid (3×50 mL) followed by phase separation 3 ppm of Rh were found in the organic phase, ie rhodium was extracted with 94% efficiency. By introduction of Texanol® to the aqueous phase followed by purification, by distillation, under standard pressure and up to a base temperature of 150° C., the ligand was deprotonized.

G) The hydroformylation of a $C_{12}$–$C_{14}$ α-olefin mixture (94 g) with rhodium catalyst/Texanol® solution from (f) (2 ppm of Rh, 100° C., 280 bar of $CO/H_2$ 1:1, 4 h) gave an olefin conversion of 98%, an aldehyde yield of 81%, and a selectivity toward linear isomers of 47% at a 6.5% balance loss (based on α-olefins; mechanical losses, formation of high-boilers and paraffin included).

Example 2

Hydroformylation with Rh/ligand 1 and separation by extraction with $CO_2/H_2O$ solution a) The hydroformylation of octene-N (isooctene mixture, degree of branching 1.3; 95 g) with rhodium/ligand 1 (13 ppm of Rh, L/Rh=10, 150° C., 280 bar of $CO/H_2$ 1:1 over a period of 5 h in 5 g of Texanol® acting as solvent) gave an octene conversion of 98%, a yield of nonanal plus nonanol of 79%, and an 18% balance loss (based on octene-N).

b) When extraction of the effluent (23 g) from 1 with the addition of 20 g of water was carried out by forcing in $CO_2$ under a pressure of one bar of $CO_2$ followed by phase separation, 4 ppm of Rh were found in the organic phase and 7 ppm in the aqueous phase. Rhodium was extracted with 85% efficiency.

c) Recycling of the rhodium complex took place as described in Example 1.

What is claimed is:

1. A process for the preparation of an aldehyde or an aldehyde and an alcohol by hydroformylation of an olefin containing more than 3 carbon atoms comprising a hydroformylation stage, in which the olefin is hydroformylated under a pressure of from 50 to 1000 bar and at a temperature of from 50° C. to 180° C. using a rhodium catalyst dissolved in a homogeneous reaction medium and a catalyst recovery stage involving extraction of the rhodium catalyst wherein:

(a) the hydroformylation is carried out in the presence of a rhodium complex, which has as ligand, a polydentate, organic nitrogen compound that is free from phosphorus and capable of forming complexes with Group VIII metals, which additionally contains at least one tertiary nitrogen radical that is capable of being protonized by a weak acid, (b) the effluent of the hydroformylation stage is subjected to extraction with an aqueous solution of a distillable acid, optionally following separation or partial separation of aldehyde and alcohol, (c) the aqueous acid extract is subjected to thermal treatment in the presence of an organic solvent or solvent mixture which is inert under the hydroformylation conditions, whereby the aqueous acid is distilled off and said complex is deprotonized and transferred to the organic phase, and (d) the organic phase containing the catalyst complex is recycled to the hydroformylation stage.

2. A process as defined in claim 1, wherein a distillable acid is used the ammonium salts of which can be redissociated into free ligand and free acid at a temperature between room temperature and 200° C.

3. A process as defined in claim 1, wherein said ligand has the formula I:

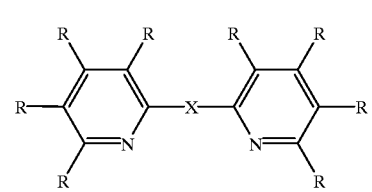

in which X denotes a bridging member selected from the group consisting of a covalent bond, methylene, ethylene, oxo, thio, alkylimino, and arylimino and the radicals R independently denote hydrogen, an alkyl radical containing from 1 to 18 carbon atoms, or an alkoxy radical containing from 1 to 18 carbon atoms, where these radicals may be part of a saturated or unsaturated ring and where at least one of the radicals R or, optionally, a substituent on said saturated or unsaturated ring formed by said alkyl or alkoxy radicals may be a radical of the formula II:

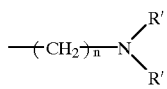

in which n is an integer from 0 to 20 and R' denotes an alkyl, cycloalkyl, aralkyl, or aryl radical containing not more than 18 carbon atoms, where the radicals R' may be bridged.

4. A process as defined in claim 1, wherein said ligand is a polyamine of the formula III:

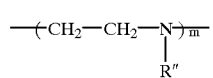

in which R" denotes hydrogen, an alkyl, cycloalkyl, aryl, or aralkyl radical, which can in turn carry a dialkylamino radical, and m is an integer from 2 to 35000, provided that when R" denotes hydrogen at least some of the hydrogen atoms are substituted by alkyl carbonyl containing from 2 to 18 carbon atoms or by a hydroxy(alkoxy)alkyl radical obtained by reaction of the secondary amino group with from 1 to 10 mol of ethylene oxide or from 1 to 10 mol of propylene oxide, and further provided that the polyamine contains at least 3 tertiary nitrogen atoms capable of being protonized.

5. A process as defined in claim 3, wherein said ligand is a bipyridine of the formula IV:

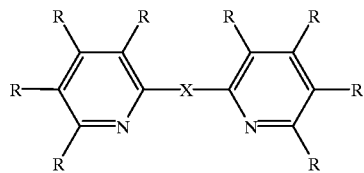

in which at least one of the radicals R or, optionally, the substituents on said saturated or unsaturated rings is a tertiary amino group-containing radical of the formula II:

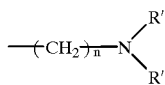

in which n and R' have the meanings stated in claim 3.

6. A process as defined in claim 1, wherein the ligand used is a compound of the formula:

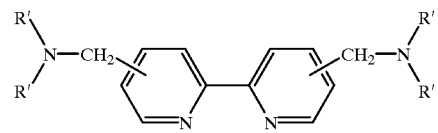

in which the radical:

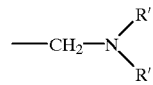

is attached to the pyridyl ring in position 4,4' or 5,5' and in which the radicals R' independently denote an alkyl, cycloalkyl, aralkyl, or aryl radical containing not more than 18 carbon atoms.

7. A process as defined in claim 1, wherein the extraction is carried out using an acid having a pK value of from 3 to 6.

8. A process as defined in claim 1, wherein the extraction is carried out using an aqueous solution of carbonic acid, formic acid, acetic acid, propionic acid, n-butyric acid, or n-valeric acid.

9. A process as defined in claim 1, wherein an olefin containing from 7 to 20 carbon atoms or polyisobutene is hydroformylated.

* * * * *